(12) United States Patent
Amin et al.

(10) Patent No.: US 9,165,097 B2
(45) Date of Patent: Oct. 20, 2015

(54) PROGRAMMABLE MICROFLUIDIC SYSTEMS AND RELATED METHODS

(71) Applicant: Purdue Research Foundation, West Lafayette, IN (US)

(72) Inventors: Ahmed Mohamed Eid Amin, Wheeling, IL (US); Mithuna Shamabhat Thottethodi, West Lafayette, IN (US); Terani Nadadoor Vijaykumar, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 13/790,865

(22) Filed: Mar. 8, 2013

(65) Prior Publication Data

US 2013/0239082 A1    Sep. 12, 2013

Related U.S. Application Data

(60) Provisional application No. 61/608,454, filed on Mar. 8, 2012.

(51) Int. Cl.
| | | |
|---|---|---|
| *G06F 17/50* | (2006.01) | |
| *G01N 35/00* | (2006.01) | |
| *G05B 19/042* | (2006.01) | |
| *B01L 3/00* | (2006.01) | |
| *G01N 35/10* | (2006.01) | |

(52) U.S. Cl.
CPC ........ *G06F 17/5027* (2013.01); *G01N 35/0092* (2013.01); *G05B 19/0426* (2013.01); *B01L 3/5027* (2013.01); *G01N 35/1097* (2013.01); *G01N 2035/00158* (2013.01)

(58) Field of Classification Search
CPC .......... G06F 17/5027; G05B 19/0426; G01N 35/0092; G01N 35/1097; G01N 2035/00158; B01L 3/5027
USPC .......................... 716/101–105, 116, 117, 139
See application file for complete search history.

(56) References Cited

U.S. PATENT DOCUMENTS

| | | | | |
|---|---|---|---|---|
| 8,226,908 | B2 * | 7/2012 | Zucchelli et al. | 422/506 |
| 8,396,701 | B2 * | 3/2013 | Ludwig | 703/13 |
| 8,594,848 | B2 * | 11/2013 | Ludwig | 700/266 |
| 8,685,325 | B2 * | 4/2014 | Wang et al. | 422/81 |
| 8,746,285 | B2 * | 6/2014 | Hong et al. | 137/897 |
| 2011/0247938 | A1 * | 10/2011 | Wang et al. | 204/603 |
| 2012/0000777 | A1 * | 1/2012 | Garrell et al. | 204/451 |
| 2013/0061962 | A1 * | 3/2013 | Kornilovich et al. | 137/565.17 |
| 2013/0118903 | A1 * | 5/2013 | Becker et al. | 204/547 |
| 2014/0045704 | A1 * | 2/2014 | Jovanovich et al. | 506/2 |

OTHER PUBLICATIONS

Aquacore: A Programmable Architecture for Microfluidics, by Ahmed M. Amin, Mithuna Thottethodi, T. N. Vijaykumar, ISCA 2007.*

* cited by examiner

*Primary Examiner* — Nha Nguyen
(74) *Attorney, Agent, or Firm* — Purdue Research Foundation

(57) ABSTRACT

A microfluidic device is programmable so that a single microarchitecture design can run many assays. Specifically, the programmable microfluidic device includes an execution method to facilitate translating from a programming language to a set of requests that are specified for the device. In addition, the microfluidic device includes a contamination mitigation method that includes a conflict list to mitigate contamination effects within the microfluidic device.

20 Claims, 8 Drawing Sheets

200

400

```
MOVE,move incubator1 to A,incubator1s1,10110111110011100110111,1,3,1,500,0,0,0
```

The individual fields in the example above, in order, are:

- MOVE:  Instruction
- move incubator1 to A:  Comment
- incubator1s1:  identifier
- 10110111110011100110111:  bit string for all the valves on the chip. 1 indicates a closed valve (pressure) and 0 indicated an open valve (vacuum)
- 1,3,1:  pump values (0: closed, 1: forward pumping, 2: reverse pumping, 3: all valves in the pump open)
- 500:  number of actuations. If pumps are off it indicates a time duration (e.g., for incubation)
- 0,0:  position sensor control (0: ignore, 1: wait until a fluid is at sensor location, 2: wait until fluid leaves sensor location)
- 0:  heater (0: off, 1: on)
- 0:  temperature (if heater is on)

```
1  ASSAY Glucose START
2  fluid Glucose, Reagent, Sample;
3  fluid a, b, c, d, e;
4  VAR Result[5];
5  input Glucose 50;
6  input Reagent;
7  input Sample 30;
8  conflict Sample FOLLOWS Glucose WASH water;
9  a=MIX Glucose AND Reagent IN RATIOS 1 : 1 FOR 10;
10 SENSE OPTICAL it INTO Result[1];
11 b=MIX Glucose AND Reagent IN RATIOS 1 : 2 FOR 10;
12 SENSE OPTICAL it INTO Result[2];
13 c=MIX Glucose AND Reagent IN RATIOS 1 : 4 FOR 10;
14 SENSE OPTICAL it INTO Result[3];
15 d=MIX Glucose AND Reagent IN RATIOS 1 : 8 FOR 10;
16 SENSE OPTICAL it INTO Result[4];
17 e=MIX Sample AND Reagent IN RATIOS 1 : 1 FOR 10;
18 SENSE OPTICAL it INTO Result[5];
19 END
```

```
1  Glucose{
2  --input s3,ip3 ;Glucose;
3  --input s4,ip4 ;Reagent;
4  --input s5,ip5 ;Sample;
5  --washport w1      ;
6  move mixer1, s3,4.47;
7  move mixer1, s4,4.47;
8  mix mixer1, 10;
9  move sensor2, mixer1;
10 sense.OD sensor2, Result(1);
11 move mixer1, s3,2.98;
12 move mixer1, s4,5.96;
13 mix mixer1, 10;
14 move sensor2, mixer1;
15 sense.OD sensor2, Result(2);
16 move mixer1, s3,1.79;
17 move mixer1, s4,7.15;
18 mix mixer1, 10;
19 move sensor2, mixer1;
20 sense.OD sensor2, Result(3);
21 move mixer1, s3,0.99;
22 move mixer1, s4,7.95;
23 mix mixer1, 10;
24 move sensor2, mixer1;
25 sense.OD sensor2, Result(4);
26 wash w1;
27 move mixer1, s5,4.47
28 move mixer1, s4,4.47;
29 mix mixer1, 10;
30 move sensor2, mixer1;
31 sense.OD sensor2, Result(5);
}
```

FIG. 7B

PROGRAMMABLE MICROFLUIDIC SYSTEMS AND RELATED METHODS

CROSS-REFERENCE TO RELATED APPLICATIONS

The present application claims priority to U.S. Provisional Patent Application No. 61/608,454 filed Mar. 8, 2012, the disclosure of which is hereby incorporated by reference in its entirety.

STATEMENT CONCERNING FEDERALLY SPONSORED RESEARCH

This invention was made with government support under CCF0726821 awarded by the National Science Foundation. The government has certain rights in the invention.

FIELD OF THE INVENTION

The invention relates to the field of microfluidics. More particularly, the invention is directed to a microfluidic device that is programmable so that a single microarchitecture design can run many assays. The programmable microfluidic device facilitates the translation from a programming language to a set of requests that are specified for the device. In addition, the microfluidic device utilizes conflict list to mitigate contamination effects within the microfluidic device.

BACKGROUND OF THE INVENTION

Microfluidics is a branch of engineering that deals with small quantities of fluids, (for example, nano or pico liters). A lab-on-a-chip (LoC) is one type of microfluidic device that enables miniaturization and integration of biological and chemical analyses to a single chip comprising a variety of channels, valves, mixers, heaters, separators, and sensors. These miniature instruments appear to offer the rare combination of faster, cheaper, and higher-precision analyses compared to conventional bench-scale methods.

Using these devices, molecules, fluids, and cells have been manipulated with precision and accuracy not achieved before. LoCs have been designed for applications in diverse domains such as proteomics, genomics, biochemistry, virology, chemical synthesis, and cell biology which are of interest to chemical, pharmaceutical, environmental and security monitoring, clinical diagnostics and food industries as well as to academic researchers in life sciences.

To date, LoCs have been designed as application-specific lab-on-a-chip (ASLoC) where a new LoC is designed for every assay by creating and connecting on-chip hardware components to match the steps of the assay, which is the detailed step-by-step specification of a particular analysis (i.e., assays are fluidic algorithms). This application-specific approach has two limitations. First, there is considerable design effort, turn-around time, and cost. Performing an experiment requires the time-consuming process of designing, fabricating, and testing a chip before conducting the actual experiment. This prolonged cycle can take months to complete, increasing effort and cost and reducing productivity. Similarly, minor modifications to an assay protocol re-incur the overheads of the design cycle. Second, the tight coupling between the LoC and the assay reduces the productivity of both LoC users (e.g., biologists, chemists, and drug developers) and LoC engineers by requiring cross-disciplinary knowledge (i.e., the engineers must know the assay details and the users need to know the constraints of the specific LoC technology).

There is a need to reduce or eliminate significant design effort, turn-around time, and cost, as well as designer degradation and user productivity through a programmable microfluidic device that can be programmed to run many assays. The invention satisfies this need.

SUMMARY OF THE INVENTION

The programmable microfluidic device has obvious advantages over application-specific lab-on-a-chip (ASLoC) of faster turn-around time, lower cost, and higher productivity for both LoC engineers and users. For purposes of this application, the term "microfluidic device" (also referred to as "programmable microfluidic chip" and "programmable lab-on-a-chip" or "PLoC") includes all microfluidic and nanofluidic devices (also referred to as "chips") that integrate more than one hardware component onto the same device/chip.

According to the invention, a programmable microfluidic chip comprises a method to facilitate translating from a programming language to a set of requests that are specified for the chip, referred to as "execution method". The hardware components of the system are controlled by the software execution method, which may run on a PC or on an embedded microcontroller. The execution method comprises a description file that comprises information regarding hardware components of the programmable microfluidic chip such as type and number of hardware components. Microfluidic device hardware components include reservoirs, fluidic functional units, and channels.

Reservoirs are basic hardware components with support to store fluids and dispense volumes of fluids and are relatively simple to implement. Fluidic functional units execute primitive operations and comprise a mixer, a heater, a separator, a sensor, a detection unit, an actuator, a valve, a pump, an incubation chamber, a reaction chamber, a separation unit, a control unit. Channels provide the connectivity among the hardware components of the microarchitecture to route fluids among the reservoirs and fluidic functional units as required.

More specifically, the fluidic functional unit that is a mixer can be any mixer ranging in sophistication from simple, passive structures that permit routing of two or more fluids into reaction chambers/channels in which mixing occurs by diffusion or simply by flowing together to more sophisticated, active mixers that include micro-electro-mechanical agitator mechanisms or pumps to accelerate mixing.

A heater allows heating and incubation at specified temperatures, and thermal cycling which are commonly used in many assays. Specifically, heaters may be resistive heaters, thin-film heaters, ceramic heaters, or incubation chambers.

A separator or separation unit separates fluids into elements based on affinity, size, weight, charge and/or hydrophobicity. Separators perform equivalently to or better than conventional laboratory devices.

A control unit controls external devices such as a digital/analog input/output.

Detection units and sensors can perform a variety of functions including measuring/sensing a physical or electrochemical property of a fluid, detecting the optical density of a mixture at certain wavelengths and measurement of fluorescence. Another function of detection units and sensors may be temperature sensing such as that of a resistance temperature detection unit or thermocouple. Some sensors may require functionality that does not enable the sensors to be miniaturized. Therefore, while some sensors have been integrated on chip, others remain off-chip. Off-chip sensing can be done by exposing fluids to external sensors using on-chip or off-chip pumps or by deploying electro-spray dispensers that spray fluid into external sensors.

A reaction chamber is where a transformation may occur and a separation unit divides materials or fluids.

Valves allow dynamically changing the connectivity among the hardware components of the microarchitecture as required by different instructions under execution. Valves include microvalves and latching valves. It is contemplated that the valves open or close depending on where there is vacuum or pressure at the control input provided by off-chip solenoid pumps. A latching valve maintains its open or closed state for a long time (e.g., a minute) even when disconnected from its pump. It is also contemplated that the valves can be arranged to function as peristaltic pumps (different from solenoid pumps) along a channel. The idea is to place three inter-locking valves along the channel. Opening a valve creates a vacuum in the valve's chamber and closing creates pressure.

The valves are opened and closed in a sequence such that vacuum and pressure are created at the right valves, moving the fluid in the required direction. Instead of using peristalsis, an electric field can be used to move fluid—i.e., droplets—by collapsing the surface tension of the droplets causing the droplet to tumble. This is known as electro-wetting. Another option is to use high-voltage electrodes to drive fluids electrokinetically.

A sequence of instructions (otherwise referred to as "sequence of statements", "set of instructions" or "instruction set") is one or more high-level programming language statements (otherwise referred to as simply "statements"). The set of instructions is received, wherein the set of instructions is a file such as one or more text files. The set of instructions and the hardware components of the programmable microfluidic chip are interfaced by mapping each statement of the sequence to a single state of hardware components including a duration to maintain the single state. The mapping can be achieved by a myriad of ways such as lookup via tables, trees, hash tables, or software code to name a few. The sequence of statements is executed by parsing the file. The hardware components of the programmable microfluidic chip are triggered and external instrumentation connected to the system is activated. The external instrumentation can be anything that is required or facilitates the assay, for example, sensors, cameras, microscopes and/or microscope stages.

The set of instructions can be any action, for example, setting up a fluidic path, actuating a pump, effecting a fluidic functional unit, and receiving data from a fluidic functional unit. Each statement corresponds to one or more bit strings, each of which designates the status of each reservoirs, fluidic functional units, and channels. For example, the bit string is a value that designates closed and open valves, the pump value of each pump such as a closed pump, an open pump, an open pump with a forward pumping action, an open pump with a reverse pumping action, number of actuations of a pump, pump stroke sequence and a pump frequency. The bit string also designates a sensor control such as ignore, wait until a fluid is at sensor location, and/or wait until fluid leaves sensor location. The bit string can include a threshold value and a determination can be made as to whether a sensor value exceeds the threshold value or fails to meet the threshold value. Each statement of the sequence runs for a defined time period.

During execution of high-level programming language statements, an issue related to fluid contamination may arise. Fluid contamination arises because fluid flow is not perfect and leave residue in the microfluidic device's hardware components. Despite efforts to reduce residue, contamination is inevitable with the reuse of reservoirs, fluidic functional units or channels, either within steps in the same assay or between different assays. For example, the residue may contaminate the next fluid that uses the same hardware component.

The invention also includes a method to mitigate contamination effects within the microfluidic device. The contamination mitigation method receives a sequence of instructions and a conflict list. Each entry in the conflict list specifies contamination caused by a specific fluid consecutively using a hardware component after another specific fluid and a washer fluid that mitigates the contamination. Again, hardware components include, for example, a mixer, a heater, a separator, a sensor, a detection unit, an actuator, a valve, a pump, an incubation chamber, a reaction chamber, a separation unit, a control unit. The sequence of instructions is analyzed by tracking each hardware component used by the fluids in each instruction of the sequence. Information regarding different fluids using the same hardware component is obtained. The information regarding different fluids using the same hardware component is checked against the conflict list to establish when contamination occurs. To alleviate contamination, a wash instruction is inserted in the sequence of instructions (or statements) between every pair of contaminating fluids. If contamination cannot be alleviated, an error is flagged. The wash instruction specifies the washer fluid and a washer fluid port. It is also contemplated that the sequence of instructions is reordered to circumvent contamination without affecting the execution correctness. Likewise, to reduce contamination, a fluid can be mapped to the same hardware components each time that fluid is used so that contaminating fluids use different hardware components as much as possible.

The described embodiments are to be considered in all respects only as illustrative and not restrictive, and the scope of the invention is not limited to the foregoing description. Those of skill in the art will recognize changes, substitutions and other modifications that will nonetheless come within the scope of the invention and range of the claims.

DESCRIPTION OF THE DRAWINGS

FIG. 4 illustrates a sequence of instructions according to one embodiment of the invention.

FIG. 7A illustrates a program for a glucose assay according to one embodiment of the invention.

FIG. 7B illustrates compiled instructions for a glucose assay according to one embodiment of the invention.

The preferred embodiments of the invention will be described in conjunction with the appended drawing provided to illustrate and not to the limit the invention, where like designations denote like elements, and in which:

DETAILED DESCRIPTION OF THE PREFERRED EMBODIMENT

Although a number of embodiments of the invention will be described in the following, it is understood that these embodiments are presented by way of example only, not limitation. The detailed description of the exemplary embodiments of the invention should not be construed to limit the scope or breadth of the invention.

To put the execution method and contamination mitigation method of the invention into context, one embodiment of a microfluidic device microarchitecture is described. There are four layers to the microfluidic device microarchitecture: a control layer, thin membrane layer, fluid layer, and electrode layer. Similar to microprocessors, many options exist to connect the fluidic functional units, from point-to-point interconnects to shared channels. Fluid routing and control is achieved by microfluidic valves, and fluid flow is achieved by peristaltic pumps.

Figure 1:
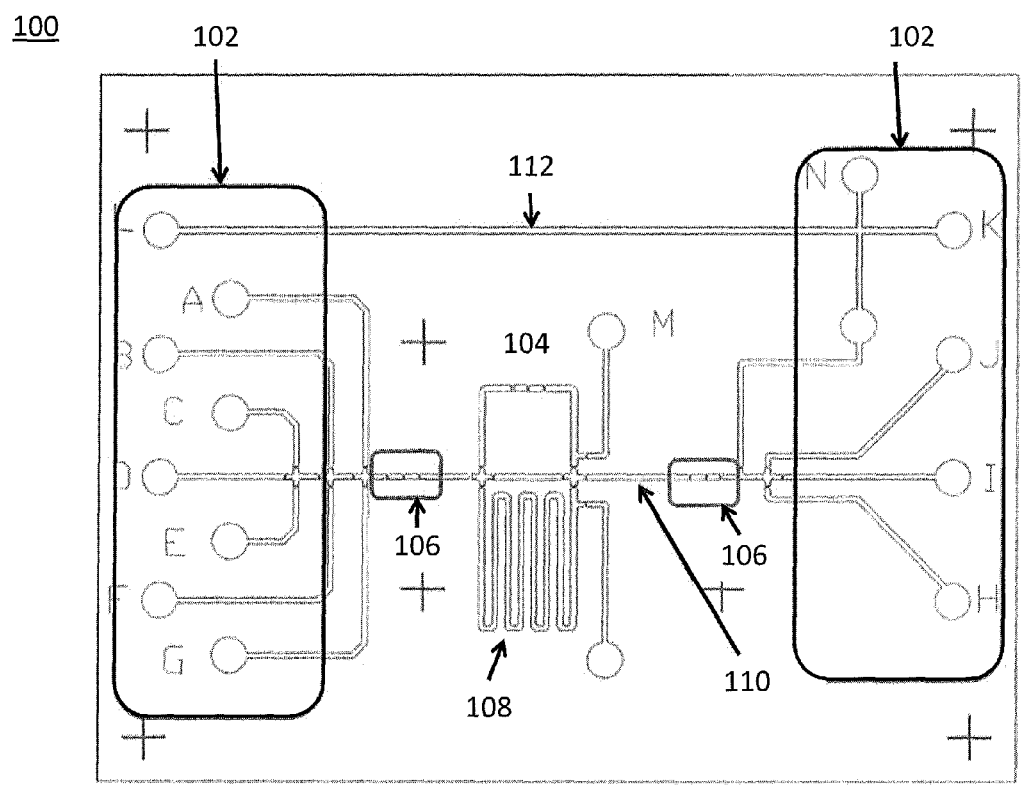
FIG. 1 illustrates the architecture of a fluid layer for a microfluidic device according to one embodiment of the invention.

FIG. 1 shows the architecture of the fluid layer 100 for a microfluidic device. The fluid layer 100 includes reservoirs, fluidic functional units, and channels. Specifically, the microfluidic device includes two reservoir sets 102. Fluidic functional units include a mixer 104, pumps 106, an incubator 108, and a sensor window 110. Also shown is a channel 112.

Figure 2:
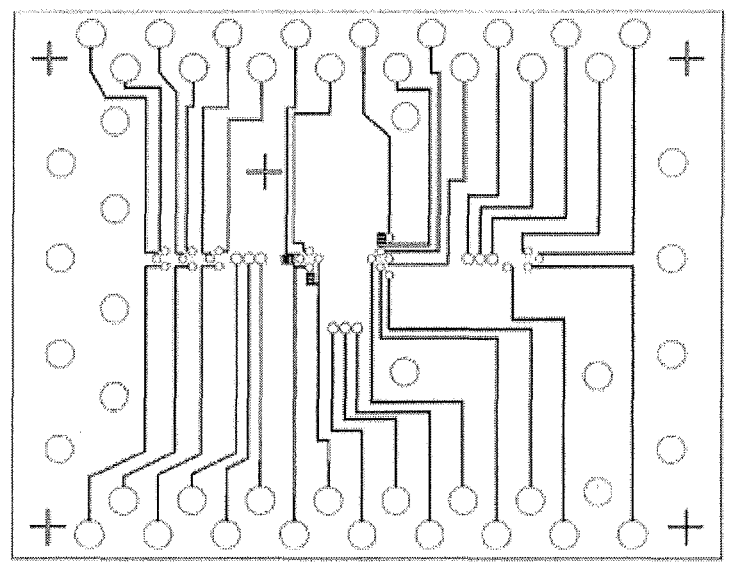
FIG. 2 illustrates the architecture of a control layer for a microfluidic device according to one embodiment of the invention.

FIG. 2 illustrates the control layer 200. The control layer 200 is positioned above the fluid layer 100 and electrode layer 300.

Figure 3:
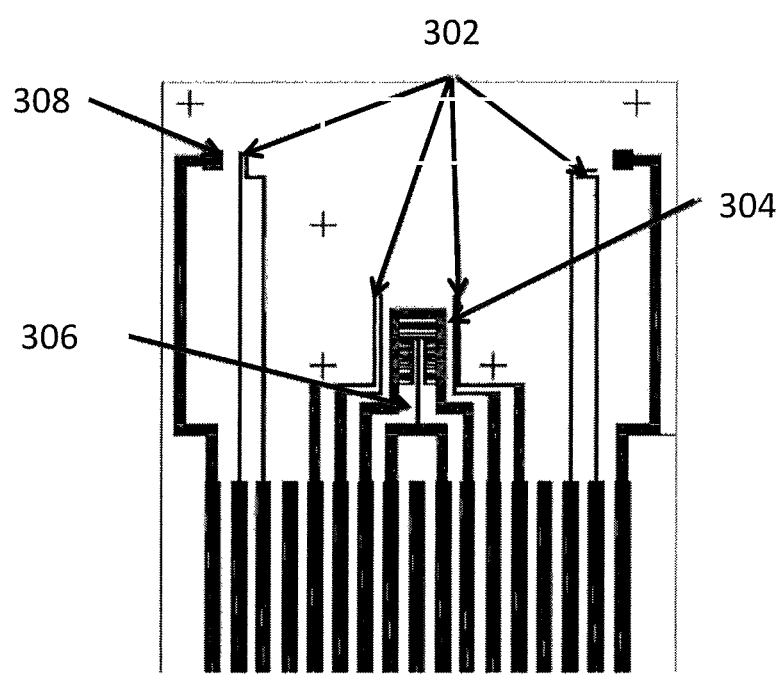
FIG. 3 illustrates the architecture of an electrode layer for a microfluidic device according to one embodiment of the invention.

FIG. 3 illustrates the electrode layer 300 used to integrate more fluidic functional units such as heaters and temperature sensors. As shown, the electrode layer 300 includes position sensors 302, a heater 304, a resistance temperature detection unit (RTD) 306, and high-voltage electrodes 308 to support capillary electrophoresis.

The hardware components of the microfluidic device are controlled by a software execution method, which may run on a PC or on an embedded microcontroller. To control the FFUs, and to abstract these control requirements into simple primitives for the execution method, a simple control platform was designed. Since each microfluidic valve requires either pressure or vacuum to close or open it, each microfluidic valve was connected to an off-chip solenoid valve. The solenoid valves were in turn connected to a pressure source, a vacuum source and an electric control signal. A high voltage at the solenoid control connects the pressure source to the microfluidic valve while a low voltage connected the microfluidic valves to a vacuum. Because pumps consist of three valves, a similar arrangement was used to control the pumps. Because solenoid valves require high voltage and current for control, and because the control is best at being computer-controlled and automated, a relay board was used to interface the computer to the solenoid valves.

Given the large number of valves, hence the large number of solenoid valves and control lines (tubes for applying pressure/ vacuum) feeding into the microfluidic chip, an interface was designed between the solenoids and the microfluidic chip. To easily exchange chips (e.g., after use), or to test new chip designs, a manifold was designed that was connected to all the tubes from the solenoids. The tubes were connected to internal holes that were routed to the bottom of the manifold, for easy alignment with the holes on top of the microfluidic chip.

To orchestrate control of the chip and to read signals from on-chip sensors under program control, an execution method was implemented. The execution method is, in its simplest form, analogous to the control unit of a microprocessor that executes microcode, acting as an interface between instructions or high-level programming language statements and hardware components. This added level of abstraction allows high-level programming language statements to be ported across different hardware components. In one embodiment, the execution method includes a file that may be one or more text file(s), which may be analogous to a computer "binary" file. The execution method is implemented as an interpreter that reads the file, where one or more lines represent a single state of FFUs including valves and pumps along with a duration to maintain that state.

The current invention proposes a runtime system and assembler that facilitates the process of translating from a programming language to a set of requests. While the process is similar to assemblers for conventional computers, the target platform-microfluidic chips—introduces a lot of differences in the translation process. Our approach would work for multiple classes of multi-purpose chips in the translation process, and not a single specific chip.

The proposed compiler and optimization passes will compile an assay into the low-level instruction set language, which is interpreted, decoded, and executed. Each instruction results in one or more of the following actions:

Setup a fluidic path by asserting the control signal of solenoid valves to open the microfluidic valves in that path, and closing the rest Actuate a microfluidic peristaltic pump for one or more pump strokes Drive a fluidic functional unit, such as driving a current in an embedded heater to increase temperature Receive signals from functional units such as temperature sensors or fluorescence sensors There is a significant difference between the actions taken for different instructions during execution. Extending the instruction set (e.g., to add support for a new functional unit) requires a significant effort to modify the runtime system. An efficient, modular, and scalable solution is required to orchestrate program execution. We propose to use a method similar to "microcode" employed in microprocessors, which we call MISTifyer. MISTifyer is essentially a lookup table, where each instruction has an entry that consists of a sequence of microinstructions. Each individual action described would be a micro-instruction in a MISTifyer entry. Micro-instructions are executed sequentially, where each micro-instruction has 1) an "action" field (e.g., switch on specific valves), 2) a "complete" field which indicates when to advance to the next micro-instruction, and 3)a maintenance" field (a pointer to subroutine that performs more complex tasks, similar to an interrupt call in computers).

In certain embodiments, an AIS assembler assembles AIS code into micro-instructions that are interpreted by a runtime system. To simplify the runtime system design and implementation, the runtime system interprets instructions that represent a single state of valves, pumps, or FFU configurations. Further, minimal flow control is currently supported. Therefore, the assembler converts instructions into micro-sequences and unrolls loops, eliminating as much control flow as possible. For example, the AIS instruction "move mixer1, s1, 10", which moves fluid from reservoir s1 to mixer1, is actually comprised of a series of micro-instructions:

(a) move the fluid from reservoir s1 to mixer1 input (position sensor) (2) meter 10 units of fluid into mixer 1 (3) return to s1 (or dispose of waste) any excess fluid in the channel.

The assembler is built using standard, well-known techniques, from lexical analysis, parsing and code generation. To aid the assembler in generating the correct code for the intended chip microarchitecture, a back-end configuration file describes the connectivity between different ports, reservoir and FFUs. For example, the configuration file would list the fluid path between reservoir s1 and mixer 1 as a string of 1s and 0s that represent the valve states (open/closed) and the pump directions that would allow fluid to flow from s1 to mixer 1. The path between mixer1 and s1 would have the same valve state, but the pump directions would be reversed.

Each line is considered a high-level programming language statement (otherwise referred to as "statement"), while a sequence of statements (or lines) represent a sequence of instructions (otherwise referred to as "sequence of statements", "set of instructions" or "instruction set"). This minimalist execution method allows portability across different chips, and to execute on very basic microcontrollers. An example of a sequence of instructions is shown in FIG. 4. In addition to the values shown in the sequence of instructions in FIG. 4, global variables may also be included such as pump stroke sequence, pump frequency (or delay interval if pumps are off), heater proportional-integral-derivative (PID) controller values, RTD parameters, sensor parameters, and digital/analog input/output. Each line of the high-level programming language statements is parsed and the corresponding relays, sensors, electrical controls are activated.

Figure 5:
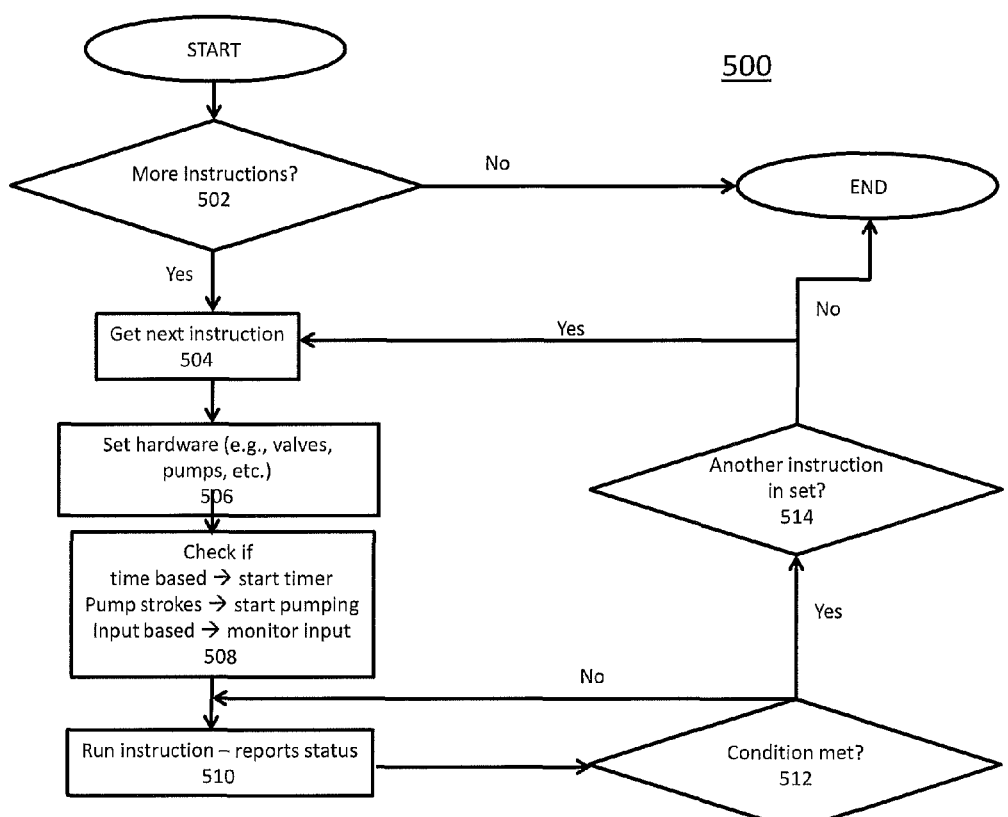
FIG. 5 is a flow chart directed to executing an instruction set according to one embodiment of the invention.

FIG. 5 is a flow chart directed to executing an instruction set 500 according to one embodiment of the invention. The execution method determines the number of statements in an instruction set. After reading the first statement, the method determines if the instruction set has another instruction at step 502. If there is not another instruction, the execution method ends. If, however, there is another instruction, the execution method retrieves the next instruction at step 504. At step 506, the execution method sets the hardware components of the microfluidic device such as valves, pumps, heaters, etc. At step 508, the execution method completes the actions as specified in the statement. For example, a timer may need to be started, a pump may need to stroke a specified number of times, or an input needs to be monitored. After the statement is run, the status is reported to the execution method at step 510. If the statement was not successfully completed at step 512, step 510 repeats and the instruction is run again and the status reported. Once the statement is successfully executed at step 512, the execution method makes a determination as to whether or not there is another statement in the instruction set at step 514. If there is another instruction at step 514, the execution method returns to step 504 and the next instruction is retrieved. If there is no additional instruction at step 514, the execution method ends.

Figure 6:
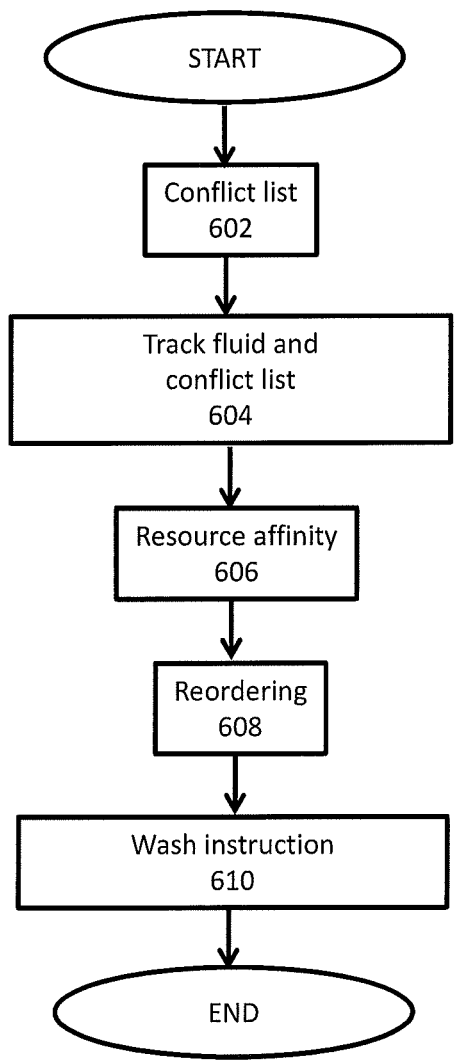
FIG. 6 is a flow chart directed to the integration of the different passes for contamination management according to one embodiment of the invention.

During execution of the sequence of instructions, an issue related to fluid contamination may arise. The invention includes a method to mitigate contamination effects within the microfluidic device. The microfluidic device has no specific target assay or knowledge of specific cross-contaminating fluids and is designed to share the same hardware component among multiple fluids of a given assay. Minor amounts of contamination are not a concern for most assays but for others contamination may cause correctness and performance problems to varying extent (e.g., assays using live cells and acid). Since fluids are heterogeneous and contamination from residue cannot be corrected, the invention uses extra wash instructions to flush the required hardware components with a cleansing fluid or washer fluid. It is also contemplated that the set of instructions is reordered to circumvent contamination. FIG. 6 is a flow chart directed to the integration of the different passes for contamination management 600 according to one embodiment of the invention. At step 602, a high-level language conflict list captures the domain-based knowledge from the assay programmer. More specifically, the programmer specifies in the high-level assay a conflict list of fluids used (or produced) in the assay that would be contaminated by another fluid used in the assay if there is hardware component sharing in a specific order between the fluids, and a washer fluid that would mitigate contamination. It is contemplated that intermediate fluids can be identified for this purpose using variable names which can be propagated through the compiled code (one name may be used for a set of fluids with a single conflict list, such as those produced by all the instances of an instruction in a loop). The conflict list specifies chemical properties of fluids and is a high-level specification that does not burden the programmer with the details of where and among which fluids hardware component sharing actually occurs at run time. While some of the hardware components used by an instruction are bound statically (e.g., reservoirs assuming there is no renaming) other hardware components are bound only at program run time (e.g., channels in assays with statically unknown control flows). Therefore, determining which instructions actually result in hardware component sharing and cause contamination is delayed until execution.

Contamination occurs because fluid flow is imperfect and leaves residue causing contamination among fluids that use the same fluid path hardware components such as reservoirs, channels and fluidic functional units. Different types of fluid interaction require different handling.

Fluid pairs can be categorized as: (1) fluids that are not affected by contamination (e.g., similar concentrations of a particular mixture), (2) fluids that may reuse the same hardware component after washing (e.g., two different separation gels), and (3) fluids that cannot use the same hardware component even after washing (e.g., acid and cell cultures).

The first category, which is relatively common, does not require any action. For the second category, a wash instruction is added. Finally, the third category of fluids cannot share hardware components with other fluids even after washes, and can be distinguished from the second category by specifying no washer fluid. For such fluids, hardware components such as mixers and identical channels are partitioned so that certain fluids only use one partition and all the other fluids use the remaining partition. Of course, if the number of fluids that cannot share components fluids in an assay exceeds the number of hardware component instances of a microfluidic device, then the assay cannot run and a microfluidic device with more redundant hardware components is required.

Turning back to the second category described above—fluids that may reuse the same hardware component after washing—it is noted that different fluids may need different washer fluids (e.g., the washer for an acid may be different than that for an alkaline). Therefore, at step 604, fluids are tracked and their conflict lists involved with every instruction. The execution method uses the conflict list and hardware component binding of each instruction to determine whether two consecutive uses of a hardware component involve conflicting fluids. If so, the execution method inserts a wash instruction with the appropriate washer fluid immediately after the earlier of the two uses. Since the hardware components used by the last instruction are tracked, the wash fluid is moved through the same hardware components. This tracking is performed at run time by leveraging the microfluidic device's fast electronic control without being critical for performance. Using the wash instructions requires the specification of which fluids could potentially contaminate which others (including fluid ordering) and the required washer fluids as well as the identification of which instructions actually cause contamination and need wash instructions.

Step 606 is directed to resource affinity contamination control. Because the wash instructions incur latency and, in some cases, the washer fluid itself may leave residue, the number of wash instructions needs to be kept to a minimum. In addition, because contamination stems from hardware component sharing by different fluids, sharing is reduced using resource affinity where a fluid is mapped to the same hardware components for all the fluid's uses, leaving the rest of the hardware components for other fluids, thus minimizing contamination.

More specifically, a fluid's live range starts from its production (or input) and ends at its last use and is mapped to a set of hardware components (fluidic functional units and channels). Assigning a hardware component to multiple fluids requires a wash, which needs to be reduced like register spills. There are a myriad of computer register allocation schemes ranging from frequency of variable use to graph coloring which can be employed for resource affinity.

If necessary, the set of instructions can be reordered at step 608. Reordering instructions may circumvent contamination without affecting the execution correctness. Likewise, to reduce contamination, a fluid can be mapped to the same hardware components each time that fluid is used so that contaminating fluids use different components as much as possible.

At step 610, the conflict lists are used to alleviate contamination by automatically inserting wash instructions when required and automatically specifying correct washer fluid ports. The wash instruction washes the hardware components used by the previous instruction. If contamination cannot be alleviated, an error is flagged.

Discussed below are two diverse assays conducted on the same PLoC. The first is an assay for glucose level calibration and testing, and the second is a particle sorter assay.

Glucose ($C_6H_{12}O_6$) is an important energy source for living organisms, and glucose levels are a key diagnostic parameter for many metabolic disorders. To measure the glucose level in a sample, a fluorescence-based enzyme assay is used. By mixing an enzyme with a glucose-containing sample, the glucose is oxidized and a by-product of the reaction reacts with a dye to generate a color ($\lambda$=570 nm) and fluorescence (Ex/Em=535/587 nm). The generated color and fluorescence intensity is directly proportionally to the glucose concentration in the sample.

FIG. 7A illustrates a program 702 and FIG. 7B illustrates compiled instructions 704 for a glucose assay according to one embodiment of the invention. Different glucose concentrations (0 nmol/µL, 0.03 nmol/µL, 0.06 nmol/µL, and 0.09 nmol/µL) are prepared off-chip. A reaction mix consisting of enzyme, buffer and probe are also prepared. Each of the glucose concentrations and the reaction mix are input into one of the PLoC input ports. Upon execution, the reaction mix and each glucose concentration are mixed in a 1:2 ratio (approx. 200 nL:400 nL), followed by an incubation step at 37° C. Finally, the resultant fluid is transported to a sensor location, which is placed under a microscope with a detector filter. At the sensing step, the fluorescence intensity is measured and recorded. To enhance the results, additional washing steps are manually inserted between fluid flows (this process is capable of being done automatically by the assembler).

On average, the intensities for glucose concentrations of 0, 0.03, 0.06 and 0.09 nmol/µL are 135, 169, 229 and 314, respectively. For comparison, the average fluorescence intensities for background (i.e., no fluid) and the intensity of water (i.e., no glucose) are 128 and 130, respectively. The higher intensities recorded for the higher glucose-concentration samples indicate a successful mixing and incubation, and a successful assay execution.

Some assays require the separation of complex biological fluids into basic components. One method to separate fluid components by size is to use a diffusion-based H-filter. The input stream with the different sized particles is flown into the same channel with an extraction buffer. Smaller particles in the input stream diffuse more rapidly into the extraction stream, while larger particles take longer. Hence, at the end of the channel, the extraction stream contains some of the smaller particles that are originally present in the input stream. To enhance the efficiency of the separation, the remainder of the input stream is re-flown again with the extraction buffer to allow smaller particles to diffuse. By repeating this process multiple times, the original input stream has a higher concentration of large particles, and the extraction stream has a higher concentration of smaller particles. Using a PLoC, the extraction is performed "recursively", where the same chip is used to automatically perform multiple cycles of extraction.

An added advantage of using the programming interface is that adding wash steps between the extraction cycles to flush the channels and prevent cross-contamination (e.g., larger particles entering the extraction stream) was very simple (and can be automated). This assay was able to be programed and executed with minimal effort.

While the invention has been described with reference to particular embodiments, those skilled in the art will recognize that many changes may be made thereto without departing from the scope of the invention. Each of these embodiments and variants thereof is contemplated as falling with the scope of the claimed invention, as set forth in the following claims.

The invention claimed is:

1. A method to facilitate translating from a programming language to a set of execution requests for a programmable microfluidic chip, comprising the steps of:
   reading a description file that includes information regarding hardware components of the programmable microfluidic chip including a number of reservoirs, a number of fluidic functional units, and a number of channels connected to a set of external hardware instrumentation;
   receiving a program file comprising a sequence of instructions;
   generating a sequence of execution requests by translation based on the description file and the program file;
   interfacing between the set of execution requests and the hardware components of the programmable microfluidic chip by mapping each execution request of the sequence to a single state of hardware components;
   executing the sequence of execution requests;
   triggering the hardware components of the programmable microfluidic chip according to said executing step; and
   activating the external hardware instrumentation.

2. The method according to claim 1 wherein the sequence of execution requests includes one or more of: setting up a fluidic path, actuating a pump, effecting a fluidic functional unit, and receiving data from a fluidic functional unit.

3. The method according to claim 1 wherein each execution request corresponds to one or more bit strings.

4. The method of claim 3, wherein at least one bit string designates a closed or open valve.

5. The method according to claim 1 wherein each execution request includes a pump value corresponding to a pump.

6. The method according to claim 5 wherein the pump value is selected from the group consisting of a closed pump, an open pump, an open pump with a forward pumping action, and an open pump with a reverse pumping action.

7. The method according to claim 1 wherein each execution request includes a number of actuations of a pump.

8. The method according to claim 1 wherein each execution request includes a sensor control.

9. The method according to claim 8 wherein the sensor control is selected from the group consisting of ignore, wait until a fluid is at sensor location, and wait until fluid leaves sensor location.

10. The method according to claim 8 wherein each execution request includes a threshold value.

11. The method according to claim 10 further comprising a sensor value wherein the sensor value exceeds the threshold value or fails to meet the threshold value.

12. The method according to claim 1 wherein the external hardware instrumentation includes one or more sensors, cameras, microscopes, microscope stages, or a temperature control element.

13. The method according to claim 1 wherein each execution request includes one or more of a pump stroke sequence and a pump frequency.

14. The method according to claim 1 wherein a fluidic functional unit is one selected from the group consisting of a mixer, a heater, a separator, a sensor, a detection unit, an actuator, a valve, a pump, an incubation chamber, a reaction chamber, a separation unit, and a control unit.

15. The method of claim 1, wherein the mapping of each execution request of the sequence to a single state of hardware components includes a termination condition to maintain the single state.

16. The method of claim 15, wherein the termination condition may include a duration of time, an electrical signal, a sensor value, or an external hardware instrumentation trigger.

17. The method of claim 1 wherein the generated sequence of execution requests is generated using a computer, server, dedicated hardware or embedded system.

18. The method of claim 1, wherein the execution requests control the fluidic functional units using pneumatics, electrical signals, or external mechanical or electrical devices by transmitting controls signals.

19. The method of claim 18, wherein the control signals are transmitted to the fluidic functional units or external instrumentation using tubes, wires, computer networks, serial cable, parallel cable, or wirelessly.

20. The method of claim 1, wherein the hardware description file includes an enumeration of fluidic functional units, the number of each of the fluidic functional units, a description of each of the fluidic functional units, and the connectivity between the fluidic functional units.

* * * * *